US005734069A

United States Patent [19]

Toney et al.

[11] Patent Number: 5,734,069

[45] Date of Patent: Mar. 31, 1998

[54] BIODEGRADABLE AMIDOAMINOESTERS

[75] Inventors: Christopher Joseph Toney, Powell; Floyd D. Friedli, Dublin, both of Ohio

[73] Assignee: Sherex Chemical Co., Inc., Dublin, Ohio

[21] Appl. No.: 307,381

[22] Filed: Sep. 14, 1994

Related U.S. Application Data

[63] Continuation of Ser. No. 119,321, Sep. 9, 1993, abandoned, which is a continuation of Ser. No. 926,152, Aug. 5, 1992, abandoned.

[51] Int. Cl.[6] .................................................. C07C 231/00

[52] U.S. Cl. ............................ 554/51; 554/110; 554/111; 554/52

[58] Field of Search .................................... 554/110, 111, 554/51, 52

[56] References Cited

U.S. PATENT DOCUMENTS

| | | | |
|---|---|---|---|
| 2,243,980 | 6/1941 | Rheiner et al. | 554/51 |
| 4,339,391 | 7/1982 | Hoffman et al. | 260/401 |
| 4,429,859 | 2/1984 | Steiner et al. | 252/8.8 |
| 4,767,547 | 8/1988 | Straathof et al. | 252/8.8 |
| 4,795,573 | 1/1989 | Tsumadori et al. | 252/8.8 |
| 4,885,102 | 12/1989 | Yamamura et al. | 252/8.8 |
| 4,937,008 | 6/1990 | Yamamura et al. | 252/8.6 |
| 5,282,983 | 2/1994 | Yamamura et al. | 252/8.6 |

FOREIGN PATENT DOCUMENTS

| | | |
|---|---|---|
| 472178 | 2/1992 | European Pat. Off. . |
| 479608 | 8/1992 | European Pat. Off. . |
| 1 593 921 | 7/1970 | France . |
| 0 040 562 | 11/1981 | Germany . |
| 0 472 178 | 2/1992 | Germany . |
| 0 479 608 | 4/1992 | Germany . |
| 0 235 631 | 11/1985 | Japan . |
| 235631 | 11/1985 | Japan . |
| 2 204 608 | 11/1988 | United Kingdom . |

*Primary Examiner*—Marianne M. Cintins
*Assistant Examiner*—Dwayne C. Jones
*Attorney, Agent, or Firm*—Scully, Scott Murphy & Presser

[57] ABSTRACT

Compounds of the formula R—$[C(O)O(CH_2)_{1-5}]_{0-1}$—C(O)$NH(CH_2)_{2-5}$—$N(R^2)$—$(CH_2)_{2-5}$—$OC(O)R^1$ wherein R and $R^1$ are each $C_8$–$C_{22}$ alkyl or alkenyl and $R^2$ is $C_1$–$C_3$ alkyl or hydroxyalkyl, benzyl, or —$C_2H_4OC(O)R^4$ wherein $R^4$ is $C_8$–$C_{22}$ alkyl or alkenyl, and acid salts and derivatives of such compounds quaternized with methyl, ethyl or benzyl, exhibit useful fabric softening and static reduction properties, as well as biodegradability.

3 Claims, No Drawings

BIODEGRADABLE AMIDOAMINOESTERS

This is a continuation of application Ser. No. 08/119,321 filed on Sep. 9, 1993, now abandoned, which is a continuation of Ser. No. 07/926,152, filed Aug. 5, 1992, now abandoned.

BACKGROUND OF THE INVENTION

The present invention relates to new rapidly biodegradable compounds which exhibit stability upon storage. These compounds are useful as fabric softener agents with antistatic properties. The properties also render them useful in a variety of surfactants and other personal care products, and in industrial clarification applications such as those encountered in sugar processing.

Fabric conditioning for improved softening and anti-static properties is normally achieved by any of several general methods including, for example, the addition of a solid or liquid fabric softening agent to the rinse cycle of a normal wash routine; the use of a substrate impregnated with a fabric conditioner composition for use in an automatic clothes dryer where the fabric conditioning agent is transferred to the clothes while in the dryer; and the inclusion of a fabric softening agent with a detergent formulation for use in the wash cycle.

Commercial fabric conditioner formulations are most commonly based on quaternary ammonium salts. Formulations for use in the final clear water rinse, and dryer and detergent softeners, are normally based on di(fatty) dimethyl quaternary salts, for example, dehydrogenated tallow dimethyl ammonium chloride (Adogen 442, Sherex Chemical Company, Inc.) or diamidoamine quaternary (Varisoft 222, Sherex Chemical Company, Inc.) or imidazoline based quaternaries.

Within recent years, there has developed a need for fabric softening compositions with faster biodegradation. Quaternary compounds with long chain alkenyl groups interrupted by ester groups are known from e.g. French Patent No. 1,593,921. Softening compositions containing such materials are disclosed in European Patent No. 0 040 562. U.S. Pat. No. 4,767,547 purports to attain rapid biodegradation by the inclusion of ester groups in long chain substituents of quaternary ammonium compounds. Similarly, U.S. Pat. No. 4,339,391 discloses esters based on hydroxyalkylammonium quaternary salts.

The present invention provides compositions containing tertiary amines and quaternary ammonium salts which rapidly biodegrade, but are sufficiently shelf stable for commercial utility. The invention further provides tertiary amines and quaternary salts having satisfactory softening properties for rinse cycle, dryer cycle, or wash cycle use, all displaying acceptable biodegradation coupled with sufficient shelf stability.

SUMMARY OF THE INVENTION

The present invention relates to compounds of formula (1):

$$R{-}[C(O)O(CH_2)_a]_b{-}C(O)NH(CH_2)_x{-}N(R^2){-}(CH_2)_y{-}OC(O)R^1 \quad (1)$$

or the formula (2 )

$$R{-}[C(O)O(CH_2)_a]_b{-}C(O)NH(CH_2)_x{-}\overset{+}{N}(R^2)(R^3){-}(CH_2)_y{-}OC(O)R^1X^- \quad (2)$$

wherein

R is straight or branched alkyl or alkenyl containing 8 to 22 carbon atoms; or $R^1$ is straight or branched alkyl or alkenyl containing 8 to 22 carbon atoms;

a is 1 to 5;

x is 2 to 5;

b is 0 or 1;

y is 2 to 5;

$R^2$ is straight or branched alkyl or hydroxyalkyl containing 1 to 3 carbon atoms, benzyl, or $-C_2H_4OC(O)R^4$ wherein R4 is straight or branched alkyl or alkenyl containing 8 to 22 carbon atoms;

$R^3$ is H, $-CH_3$, $-C_2H_5$ or benzyl; and

X is an anion.

In another aspect, the present invention comprises formulations containing one or more of such compounds of formula (1) and/or (2).

DETAILED DESCRIPTION OF THE INVENTION

Compounds of the foregoing formulas (1) and (2) can readily be prepared from known starting materials employing conventional synthetic procedures. For instance, one intermediate that would generally be found to be available has the formula $H_2N(CH_2)_x{-}N(R^2){-}(CH_2)_yOH$, wherein x, y and $R^2$ have the meanings set forth herein. If desired, this intermediate can be obtained by hydrogenation of the product synthesized from the corresponding N-substituted alkanolamine of the formula $R^2N{-}(CH_2)_yOH$, and the corresponding alkenylnitrile $(H_2C{=}CH){-}(CH_2)_{x-3}{-}CN$. The resulting aminoalkyl-hydroxyalkyl tertiary amine is then reacted with alkenoic acids and/or fatty acids of the formula RCOOH and $R^1COOH$ to form an amide-ester. It will be recognized that R and $R^1$ can be identical, although in those instances where they are different the resulting amide-esters can comprise a mixture.

When the quaternized derivative of the thus formed amide-ester is desired, it can be prepared using conventional quaternizing techniques such as acidification with an acid of the formula HX, or reaction with a guaternizing agent such as $CH_3X$ or $C_6H_5CH_2X$.

When desired the $R^2$-substituted alkanolamine can be prepared from the corresponding primary alkanolamine by reaction thereof with e.g. benzylchloride or $R_4C(O)OC_2H_4$ chloride.

In the preferred embodiments of the present invention, R and $R^1$ each contain 14–22 carbon atoms, and each more preferably contains 16 to 18 carbon atoms; a is 3 or 4; x is 3 or 4 and more preferably 3; y is 2 or 3 and preferably 2; and $R^4$ preferably contains 14–22 carbon atoms, and more preferably contains 16 to 18 carbon atoms. The anion X is any organic or inorganic anion capable of forming compounds as described herein compatible with the desired fabric softening, static reducing, and biodegradability properties. Preferred anions include chloride, bromide, methylsulfate, ethylsulfate, acetate, lactate, sulfate and phosphate. Of these, the especially preferred anions include chloride and methylsulfate.

To synthesize those embodiments of the present invention wherein b is 1 and a is 3, the alkanoldiamine substituted with $R^2$ is reacted with e.g. butyrylactone, and the intermediate thus formed is thereafter reacted with a compound of the formula RCOOH as described herein.

Compounds having the structures described 0 hereinabove for formulas (1) or (2) can be used as is or, preferably, dispersed in aqueous formulations such that the desired amount for any particular wash load can be poured directly into the washing machine at the appropriate point during the rinse cycle. Aqueous dispersions of up to 10 weight percent, and more preferably 4–7%, of the compound of formula (1) and/or formula (2), are useful. Such formulations have been found to provide fabric softening comparable to other commercially available fabric softeners and to provide static control comparable to that of premium grade commercial fabric softeners.

Dispersions are preferably prepared by adding the compound to water, at room temperature or preferably heated, under constant agitation. Satisfactory preparation temperatures range up to about 100° F. As is known, it may be advantageous to add up to about 0.5 wt % of a dispersion aid such as $CaCl_2$ (preferably as an aqueous solution thereof). A dispersion containing up to about 5% of the compound of the present invention will exhibit the desired viscosity, that is, the viscosity of a liquid formulation which is think but pourable. Dispersions containing over about 10% by weight of the compound of the present invention risk being too thick and may gel.

The invention will be described further in the following examples. The following exemplification should be interpreted for illustrative purposes and not for purposes of limiting the scope of the invention which the applicants claim.

EXAMPLE 1

A. Preparation of 2-cyanoethyl-2-hydroxyethylmethylamine 1000.0 grams (13.31 moles) of 2-methylaminoethanol was placed in a 3000 milliliter 3-neck flask equipped with a stirrer, a condenser, an addition funnel, and a thermometer. 50.0 grams of distilled water was charged to the flask, and 705.4 grams (13.31 moles) of acrylonitrile was charged to the addition funnel (875.2 ml). The acrylonitrile was added dropwise slowly over 55 minutes, during which time the flask was air-cooled and the contents of the flask increased in temperature to about 75° C. The maximum temperature of the flask contents during the addition of the acrylonitrile was about 81° C. After the addition of acrylonitrile was completed, the flask contents were held at 75° C. while agitation was continued for another 2.75 hours. The contents were then allowed to cool to room temperature. The flask was then heated to 80° C. under 5 mm Hg vacuum, to remove residual water and acrylonitrile. The flask contents then comprised 1697.8 grams of product; GC analysis showed that 96.4% of this was the desired reaction product.

B. Formation of Diamine 852 grams of toluene and 852 grams of the 2-cyanoethyl-2-hydroxyethylmethylamine prepared in Paragraph A of this Example was charged to a 1-gallon Parr reactor followed by 34.08 grams of a wet nickel catalyst ("A-5000". available from Activated Metals). The reactor was evacuated and sealed, and then charged to 100 psig with hydrogen and heated to 100° C. After 26 minutes, during which time additional amounts of hydrogen were added, the reactor was charged to 500 psig with hydrogen, and reactor conditions became exothermic about 7 minutes later. The temperature reached 146° C. but was thereupon immediately cooled to, and maintained at, about 95°–100° C. These reaction conditions (including a total pressure of 510–520 psig) were maintained for a total reaction time of 4.5 hours from the time at which the pressure was raised to 500 psig. The reactor was then shut down, the reactor contents were cooled to room temperature, and the reactor was vented to atmosphere. The reactor contents were filtered to yield 1530 grams of product having a total amine value of 424.2. The filtered product was vacuum-stripped of solvent for about 2.5 hours at 150° F. to yield 758.44 grams of stripped product. GC Analysis: 9.95% methylaminoethanol; 2.24% nitrile from step 2(A); 76.94% title product.

Another 844 grams of toluene and 844 grams of the 2-cyanoethyl-2-hydroxyethylmethylamine made in step A of this Example were charged to a 1-gallon Parr reactor, followed by 33.76 grams of wet nickel catalyst ("A-5000"). The reactor was evacuated and sealed, and then charged to 100 psig with hydrogen and heated to 100° C. After 23 minutes, during which time additional amounts of hydrogen were added, the reactor was charged to 500 psig with hydrogen. The reactor was maintained at 100° C. for another 172 minutes, during which time the total pressure was about 530–540 psig. The reactor was then shut down, the reactor contents were cooled to room temperature, and the reactor was vented to atmosphere. The reactor contents were filtered to yield 1476 grams of product having a total amine value of 414.7. The filtered product was vacuum-stripped of solvent for about 2.5 hours at 150° F. to yield 734.69 grams of stripped product. GC analysis: 9.62% methylaminoethanol; 0.12% nitrile from step 2(A); 72.47% title product.

The two lots of vacuum-stripped product were combined to yield a final product, which had a total amine value of 773.1 and contained 75.66% of title product.

C. Distillation 1451.8 grams of the combined final product of step B was fractionated to remove residual 2-methyl-aminoethanol. Fractionation was carried out in a 2000 ml 3-neck flask equipped with an agitator and heating mantle and with a 10-tray Oldershaw column and a magnetic reflux head. Over the first 2 hours, the pot temperature steadily increased from 26° C. to 121° C. and the head temperature increased from 25° C. to 45° C. The column pressure decreased from atmospheric to about 5 mm Hg in the first 45 minutes, and then to about 0.75 mm Hg an hour later Thereafter, the pot temperature was held at 120°–125° C., and the column pressure decreased steadily to 0.40 mm Hg. The first cut of 127.7 g was taken about 5.25 hours from the beginning of the run. At this point the head temperature was raised to 65° C., and rose steadily to 75°–80° C. through the collection of the main cut. A second cut of 133.6 grams was taken at 9.75 hours from the beginning of the run. The main cut comprised the next 872.3 grams. Gas chromatography analysis of the main cut revealed that the product contained 94.57% of the desired diamine, and 0.34% methylaminoethanol.

D. Preparation of Amide Ester

To prepare the desired amide ester, 1500 grams (5.16 moles) of stearic acid "Hydrofol 1870" was charged to a 3000 ml 4-neck flask fitted with an agitator, water trap, thermometer, nitrogen sparge, and an addition funnel. "Hydrofol 1870" is a product of Sherex Chemical Company, Inc., Dublin, Ohio and comprises on the average a composition of about 68% stearic acid, about 28% palmitic acid, about 3% myristic acid, and about 1% eicosanoic acid. 340.6 grams (2.58 moles) of the main cut recovered in Step C above was charged to the addition funnel. The acid was melted at 85° C. under a nitrogen blanket. When all the acid had melted, nitrogen was sparged into the acid. Nitrogen sparge continued for about 20 minutes. The diamine was then charged to the acid gradually during which the temperature rose to about 100° C. The flask was heated further externally to about 120° C. After about 1 hour, the heat was increased to about 150° C. Over the next 3.5 hours, the temperature was gradually increased to 180° C. Water began to evolve at about 135° C. and continued to evolve thereafter. After a total of 4.5 hours from addition of the acid the heat was discontinued, and when the temperature in the flask had dropped to 100° C. the nitrogen was shut off and the reactor sealed and allowed to cool to room temperature. Subsequently, the flask contents were reheated to about 85° C. and additional diamine was added to the reaction mixture (41.3 grams). The reaction mixture was heated to 150° C., then to 180° C. After about 5.5 hours, the reaction mixture was sparged with nitrogen to carry out any excess amine and the heat was discontinued. The acid value of the flask contents at this point was 13.4.

E. Quaternization 825 grams of the ester amide produced in accordance with the preceding Step D was quaternized in accordance with the procedure described in Example 1. The reaction proceeded for another 3.25 hours, at the end of which the reactor was cooled to room temperature and vented. The reaction mixture was found to contain zero free acid, a total amine value of zero and an acid value of 0.41, indicating that essentially complete quaternization had taken place.

BIODEGRADATION

The compounds of this invention exhibit surprisingly rapid biodegradation. The compound of formula (2) wherein b is 0; x is 3; y is 2; $R_2$ and $R_3$ are methyl; R and $R_1$ are hard tallow; and X is Cl was evaluated for biodegradation according to the following scheme:

All compounds were obtained from Sherex Chemical Co. (Dublin, Ohio). The compounds with trade names parentheses were used as supplied; the others were purified by recrystallization from appropriate solvents. The bacteria were obtained as Polyseed (Polyback Corp.). Polyseed is a mixture of 12 bacteria which are characteristic of those found in waste water. HPLC grade water was used (Fisher) and dissolved oxygen was measured with a dissolved oxygen probe and meter (Yellow Springs instruments, Model 58). Biodegradation samples were incubated at 20°±0.3° C. in the dark. Absorbance measurements were carried out using a UV-Visible spectrophotometer (Hewlett Packard Model 8452A).

ACCLIMATION OF BACTERIA

A capsule containing Polyseed was dispersed into 250 ml dilution water where the oxygen level in the water was 15.0±0.2 mg/l If the oxygen level was below 15 mg/l the water used was standard APHA dilution water as described in the standard methods. The nutrient solution was prepared from 25 g peptone, 15 g beef extract, 4 g urea, 4 g glucose, and 3 g $KH_2PO_4$ dissolved into 1000 ml HPLC grade water. Over a five day period, the bacteria were given less nutrient solution and more QAC (quaternary ammonium compound) solution until the bacteria were not receiving any nutrient solution. On the first day, the bacteria were fed 1 ml of nutrient solution and 10 mg of QAC. On the second day 1 ml of nutrient solution and 20 mg of QAC was added to the culture along with 20 mg of QAC. On the fourth day 0.5 ml of nutrient solution and 80 mg of QAC was added. On the fifth day 0.2 ml of nutrient solution was added, along with 100 mg of QAC and 1 ml of diammonium phosphate solution at a concentration of 24 g/1 water. Fifty ml aliquots of HPLC water with a dissolved oxygen level of 15 mg/$O_2$/l were added to the cultures each day after the first day. After the five day period 2 ml aliquots of the bacteria are immediately used in closed bottle testing.

METHOD

The procedure used for biodegradation evaluations is a variation of the Closed Bottle of Biochemical Oxygen Demand (BOD) method. The method used is as described in Method 507 of the Standard Methods for the Examination of Waste and Wastewater (15th ed., 1980) with the following exceptions: Classically the closed bottle test has been performed with activated sludge as the source of bacteria. Polyseed is used herein to reduce the contribution of variable bacterial populations to experimental error. The bacterial composition is consistent within a lot of Polyseed and lot to lot variability was small. To eliminate any contribution to oxygen demand by organic materials in the water, HPLC grade water was used.

Acclimation of bacteria is one of the key factors in determining the biodegradability of QAC's. The bacteria used in each closed bottle test were acclimated over a five day period as noted above. When tests were repeated, new acclimated bacteria were prepared.

Each round of testing included a water control, a seed correction, a glucose/glutamic acid control, and a series of QAC's. All of the samples were incubated in the dark at 20° C. Dissolved oxygen measurements were taken periodically, typically every 5, 10, 15, 20, 25 and 28 days. Tests were considered invalid if any one of the controls failed; failure was indicated by: (1) The dissolved oxygen level in the water control changed more than 0.2 mg/l over a period of five days, or (2) the seed correction sample showed a depletion outside the range 0.6–1.0 mg/l over the same five-day period. Biochemical oxygen demand values were not calculated, rather calculations of % biodegradation were conducted using the ratios of biochemical oxygen depletion (mg $O_2$ depleted/mg sample) to calculated oxygen depletion (theoretical-based on empirical formula of primary molecule) or chemical oxygen depletion (experimental-based on elemental analysis). The above-identified compound was found to biodegrade 27% in 20 days.

What is claimed is:

1. A compound of formula (1): $[R—C(O)NH(CH_2)_2—N^+—(R^2)(R^3)—(CH_2)_2—OC(O)R^1X^-]$

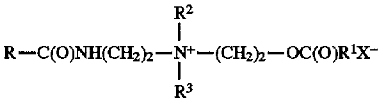

(1)

wherein

R is straight or branched alkyl or alkenyl containing 16 to 18 carbon atoms;

$R^1$ is straight or branched alkyl or alkenyl containing 16 to 18 carbon atoms;

$R^2$ $—CH_2CH(OH)CH_3$;

$R^3$ is $—CH_3$; and

X is an anion selected from the group consisting of chloride, bromide, methylsulfate, ethylsulfate, acetate, lactate, sulfate and phosphate.

2. A compound of formula (1) according to claim 1 wherein X is methylsulfate.

3. A fabric softening composition comprising one or more compounds according to claim 1 in an amount effective to impart softening to fabric.

* * * * *

UNITED STATES PATENT AND TRADEMARK OFFICE

CERTIFICATE OF CORRECTION

PATENT NO. : 5,734,069

DATED : March 31, 1998

INVENTOR(S) : Christopher J. Toney, et al.

It is certified that error appears in the above-identified patent and that said Letters Patent is hereby corrected as shown below:

On the Title Page, Section [56], under "FOREIGN PATENT DOCUMENTS", line 2:

"8/1992" should read -- 4/1992 --. and lines 5 and 6 delete the following:

--0 472 178 2/1992 Germany

0 479 608 4/1992 Germany--

Column 3, line 23: "think" should read --thick--

Column 5, line 43: "instruments" should read --Instruments--

Column 5, line 53: after "mg/1" insert --.--

Signed and Sealed this

Thirty-first Day of October, 2000

*Attest:*

Q. TODD DICKINSON

*Attesting Officer*

*Director of Patents and Trademarks*